Figure 1:
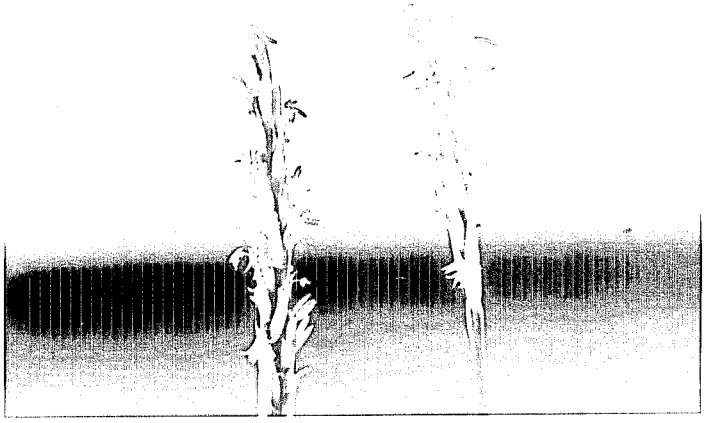

United States Patent [19]

Whiting

[11] Patent Number: Plant 6,516

[45] Date of Patent: Jan. 3, 1989

[54] ZOYSIA GRASS PLANT (ZT-4)

[76] Inventor: Hubert F. Whiting, 28252 Faircrest Way, Escondido, Calif. 92026

[21] Appl. No.: 26,140

[22] Filed: Mar. 16, 1987

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

I disclose that my herein invention of a new variety of Zoysia grass plant, was discovered by me through my cross-pollination of selected varieties of Zoysia grass plants, then through asexual repropagation, selected the new and distinct variety of Zoysia grass plant ZT-4, which produces an excellent uniform turfgrass surface from stolons and rhizomes, then held complete green color throughout two winter periods. This new variety of Zoysia grass plant produces a 40% to 50% greater stolon and rhizome growth rate at low winter temperatures. The anthers of the new claimed variety of Zoysia grass plant, are pale yellow color as defined by the ISCC-NBS centroid color chart; the stigmas are yellowish white color, as defined by the ISCC-NBS centroid color chart; the stolon internodes of the new claimed variety of Zoysia grass plant are closer together, and thinner in width. The entire plant of the new claimed variety of Zoysia grass plant, is glabrous except on the upper leaf surface which is sparsely pubescent, also on the inside of the collar just above the ligule where several long hairs are present. The electrophoresis isoenzyme banding patterns show distinct uniqueness of the new claimed variety of Zoysia grass plant designated ZT-4.

3 Drawing Sheets

The present invention and discovery relates to a new and distinct variety of Zoysia grass plant, which was developed by me through a series of cross-pollination of collected varieties of Zoysia grass plants. This cross-pollination was done by me at Fallbrook, Calif., U.S.A. about 34 degrees north latitude. I harvested seeds from this cross-pollination of selected varieties of Zoysia grass plants and planted these seeds out in germinating trays. About six weeks after the seeds germinated, I selected the one hundred most rapidly establishing plants. I then transplanted each separate seedling into one gallon containers. As these seedlings grew and developed, I once again selected the most aggressively establishing and most desirable for turfgrass potential; this left forty five seedlings, these forty five seedlings were then each individually broken up by me into small pieces of stolons. I then planted these small pieces of stolons into the soil in an area that was three feet square. When this process was completed, I had forty five individual seedlings planted in forty five three foot square plots, all asexually planted by me. The location of this transplanting was at Fallbrook, Calif., U.S.A. Once these forty five three foot square plots became established through the spreading of the planted stolons. I formed a turfgrass surface through regular mowing. I again made selections from the forty five plots. The selections I made this time were again individually transplanted by me asexually, by breaking sufficient stolon material of each separate selection to further replant the now ten selections into larger individual separate plots of ten feet by eight feet. Once these larger plots became established through the spreading of the planted stolons. I formed a turfgrass surface through regular mowing. I again made selections from these ten plots. The new claimed variety of Zoysia grass plant, is one of those selections, and which I have designated ZT-4. This new selected variety of Zoysia grass plant spread by stolons and rhizomes to produce an excellent turfgrass surface when regularly mown. I observed that this new claimed variety produced an excellent uniform turfgrass surface, which held complete green color throughout two replicated trial winter periods, when compared to the closest known variety of Zoysia grass plant which lost 25% to 30% green color, throughout these two trial periods. This new claimed variety of Zoysia grass plant ZT-4 also produced a 40% to 50% greater stolon and rhizome growth rate at low winter temperature, when compared to the closest known variety of Zoysia grass plant identified as ZT-26, which is my U.S. plant patent application Ser. No. 06/926,963 filing date 10/31/1986. During the continued asexual reproduction by stolons, I have confirmed that the above-described characteristics are transmitted through succeeding propagations, and have confirmed that the new claimed variety of Zoysia grass plant has the following unique combination of characteristics. The new and distinct variety of Zoysia grass plant is illustrated in the accompanying color photographs, with the photographs of the closest known Zoysia grass plant known as ZT-26. The most noticeable variations between the new claimed variety of Zoysia grass plant and the closest known variety of Zoysia grass plant ZT-26, is that the new claimed variety of Zoysia grass plant is a deep yellowish green color with a more dense growth characteristic and the stolon is thinner with internodes closer together; the new claimed variety of Zoysia grass plant is sparsely pubescent on the upper leaf surface, when compared to the closest known variety grass plant which is glabrous. The new claimed variety of Zoysia grass plant ZT-4 has stigmas and anthers of different color, before dehiscence, when compared to the closest known variety of Zoysia grass plant ZT-26. The new claimed variety of Zoysia grass plant ZT-4 has unique isoenzyme electrophoresis banding patterns, when compared to the closest known variety of Zoysia grass plant ZT-26.

IN THE DRAWINGS:

FIG. 1 is a photograph of two spikes taken from the same area, the spike on the right in the photograph is of the new claimed variety of Zoysia grass plant ZT-4, with the spike on the left in the photograph is of the closest known variety of Zoysia grass plant ZT-26; this photograph shows the light greenish yellow colored anthers as defined by the ISCC-NBS centroid color chart, of the closest known variety of Zoysia grass plant ZT-26, when compared to the pale yellow colored anthers of the new claimed variety of Zoysia grass plant ZT-4 as defined by the ISCC-NBS centroid color chart.

Figure 2:
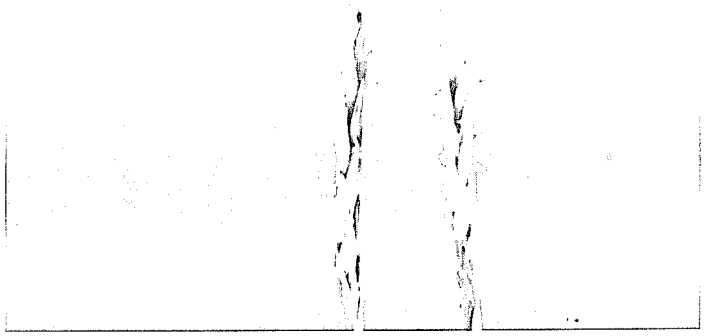

FIG. 2 is a photograph of two spikes taken from the same test area, the spike on the left in the photograph is of the closest known variety of Zoysia grass plant ZT-26, with the spike on the right in the photograph is of the new claimed variety of Zoysia grass plant ZT-4; this photograph shows the pale yellow green colored stigmas of the closest known variety of Zoysia grass plant ZT-26 as defined by the ISCC-NBS centroid color chart, when compared to the yellowish white colored stigmas of the new claimed variety of Zoysia grass plant ZT-4 as defined by the ISCC-NBS centroid color chart.

Figure 3:
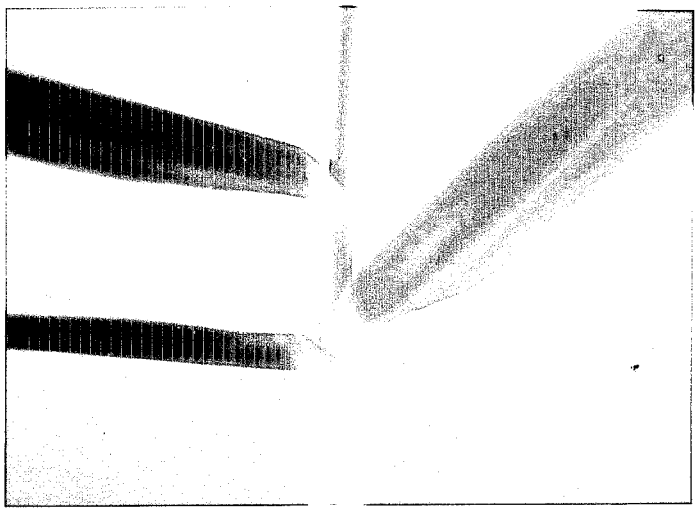

FIG. 3 is a photograph of a culm of the closest known variety of Zoysia grass plant ZT-26 taken from the same test area; this photograph shows the glabrous leaves.

Figure 4:
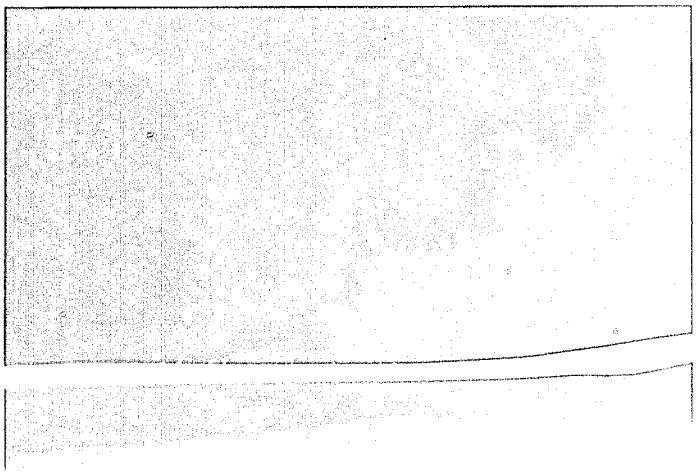

FIG. 4 is a photograph of a leaf of the new claimed variety of Zoysia grass plant ZT-4 taken from the same test area; this photograph shows the sparsely pubescent upper leaf surface. The following photographs show the electrophoresis isoenzyme banding patterns, using the phosphoglucomutase (PGM) and esterase (EST), electrophoresis and isoenzyme techniques have been documented for grass plant identification, (WU, Harivandi, Harding, and Davis).

Figure 5:
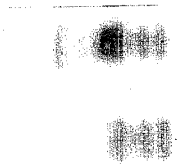

FIG. 5 this photograph shows the electrophoresis zymogram patterns of the esterase (EST) isoenzyme banding pattern, of the new claimed variety of Zoysia grass plant ZT-4 with the closest known variety of Zoysia grass plant ZT-26, both grasses taken from the same test area.

Figure 6:
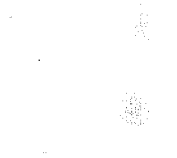

FIG. 6 this photograph shows the electrophoresis zymogram patterns of the phosphoglucomutase (PGM) isoenzyme banding pattern, of the new claimed variety of Zoysia grass plant ZT-4 with the closest known variety of Zoysia grass plant ZT-26, both grasses taken from the same test area.

Figure 7:
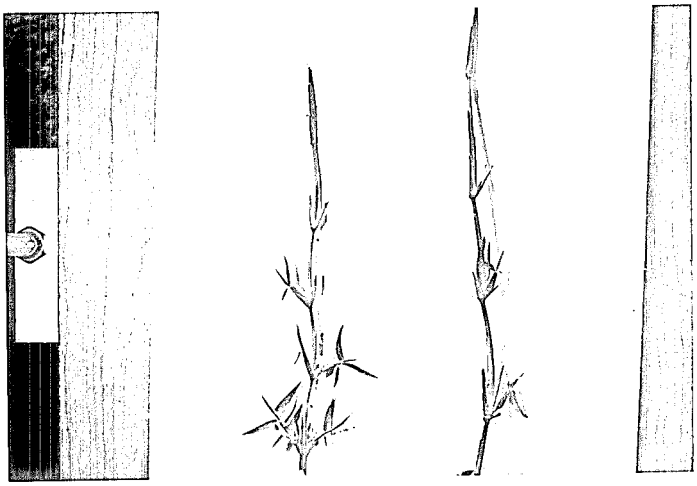

FIG. 7 is a photograph of two stolons taken from the same test area; this photograph shows the stolon on the left in the photograph of the new claimed variety of Zoysia grass plant ZT-4 with internodes closer together and the stolon also thinner, when compared to the closest known variety of Zoysia grass plant ZT-26, which is on the right in the photograph with the stolon thicker and the internodes farther apart.

A detailed description of the new and distinct variety of Zoysia grass plant ZT-4 is:

(a) An attractive deep yellowish green color, color number 118.deep YG, of the ISCC-NBS centroid color chart.

(b) The grass is low-growing, erect in habit.

(c) The grass spreads by stolons and rhizomes, forming a dense, uniform surface, with an extensive root system; stolons 1 millimeter in width with internodes 2.5–3 centimeters apart.

(d) Culms vary in height from 18–22 centimeters.

(e) Leaves rolled in bud shoot.

(f) The leaf blade is flat, and gradually tapering to an acute point.

(g) The first mature leaf is 3–4 millimeters in width and 8–12 centimeters long.

(h) The upper leaf surface is sparsely pubescent.

(i) The ligule is a very small ciliate fringe 0.25 millimeters in height, with several long hairs just above the ligule on the inside of the collar 1–2 millimeters long.

(j) Auricles are absent.

(k) The collar is broad, and continuous.

(l) The sheath is glabrous, and split with separate margins.

(m) The entire plant is glabrous, except on the upper leaf surface and on the inside of the collar just above the ligule, where several long hairs are present.

(n) The inflorescence consists of a single spike at the top of the main stem.

(o) The spike contains stigmas of yellowish white color, color number 92.y White of the ISCC-NBS centroid color chart; the anthers are pale yellow color, color number 89.p.Y of the ISCC-NBS centroid color chart; the glumes are 2–3 millimeters long, blunt at their base, pointed at their tips.

A detailed description of the closest known variety of the species of Zoysia grass plant ZT-26 is:

(a) An attractive dark yellowish green color, color number 137.d.yG of the ISCC-NBS centroid color chart.

(b) The grass is low growing, erect in habit.

(c) The grass spreads by stolons and rhizomes, forming a dense, uniform surface, with an extensive root system; the stolons are 1.5 millimeters in width, with internodes 3.5–4 centimeters apart.

(d) Culms vary in height from 14–16 centimeters.

(e) Leaves rolled in bud shoot.

(f) The leaf blade is flat, and gradually tapering to an acute point.

(g) The first mature leaf is 3–4 millimeters in width and 5–9 centimeters in length.

(h) The leaf blade is glabrous.

(i) The ligule is a very small ciliate fringe.

(j) Auricles are absent.

(k) The color is broad, and continuous.

(l) The sheath is glabrous, except for two or three hairs at the top of the sheath at the sides of the ligule; the sheath is split with separate margins.

(m) The entire plant is glabrous, except at the top of the sheath where two or three hairs are present at the sides of the ligule.

(n) The inflorescence consists of a single spike at the top of the main stem.

(o) The spike contains stigmas of pale yellow green color, color number 121. p.YG of the ISCC-NBS centroid color chart and anthers of pale greenish yellow color, color number 104.p.gY of the ISCC-NBS centroid color chart; the glumes are 2–3 millimeters long, blunt at their base, pointed at their tips.

REFERENCE

1. Lin Wu, H. Harivandi, James A. Harding and William B. Davis. 1984. Identification of Kentucky Bluegrass Cultivars with Esterase and Phosphoglucomutase Isoenzyme Markers, Crop Science. Vol. 24 July-August 1984, P. 763–768.

I claim:

1. A new and distinct variety of Zoysia grass plant herein shown and described by a deep yellowish green color, as defined by the ISCC-NBS centroid color chart; this new claimed variety of Zoysia grass plant ZT-4 produced an excellent uniform turfgrass surface, which held complete green color throughout two randomized replicated trial winter periods, when compared to the closest known variety of Zoysia grass plant ZT-26, which lost 25% to 30% of green color throughout those two trial periods; this new claimed variety of Zoysia grass plant ZT-4 also produced a 40% to 50% greater stolon and rhizome growth rate at low winter temperatures, when compared to the closest known variety of Zoysia grass plant ZT-26; the anthers of the new claimed variety of Zoysia grass plant are pale yellow color, as defined by the ISCC-NBS centroid color chart; the stigmas are yellowish white color, as defined by the ISCC-NBS color chart; the stolon internodes of the new claimed variety of Zoysia grass plant are closer together and thinner in width than the closest known variety of Zoysia grass plant ZT-26; the entire plant of the new claimed variety is glabrous except on the upper leaf surface which is sparsely pubescent and on the inside of the collar, just above the ligule, where several long hairs are present; and the new claimed variety of Zoysia grass plant ZT-4 shows distinct uniqueness with the electrophoresis isoenzyme banding pattern methods, when compared to the closest known variety of Zoysia grass plant ZT-26.

* * * * *

Z4

Z26

Z4

Z26